(12) United States Patent
Gadol et al.

(10) Patent No.: US 12,406,771 B2
(45) Date of Patent: Sep. 2, 2025

(54) PREDICTING EFFICACIES AND IMPROVING SKINCARE TREATMENT OUTCOMES BASED ON RESPONDER/NON-RESPONDER INFORMATION

(71) Applicant: L'Oreal, Paris (FR)

(72) Inventors: Sandrine Gadol, New York, NY (US); Michelle Rathman-Josserand, La Celle Saint-Cloud (FR); Benjamin Askenazi, Clichy (FR); Panagiotis-Alexandros Bokaris, Paris (FR); Nukhet Cavusoglu, Claye-Souilly (FR); Stephanie Nouveau, Boulogne-Billancourt (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/784,079

(22) PCT Filed: Apr. 29, 2022

(86) PCT No.: PCT/US2022/027110
§ 371 (c)(1),
(2) Date: Nov. 3, 2022

(87) PCT Pub. No.: WO2022/232628
PCT Pub. Date: Nov. 3, 2022

(65) Prior Publication Data
US 2024/0221935 A1    Jul. 4, 2024

Related U.S. Application Data

(60) Provisional application No. 63/182,664, filed on Apr. 30, 2021.

(30) Foreign Application Priority Data

Jul. 23, 2021    (FR) ........................... 2108018

(51) Int. Cl.
*A61N 5/06*    (2006.01)
*A61B 5/00*    (2006.01)
*G16H 50/20*    (2018.01)

(52) U.S. Cl.
CPC ............. *G16H 50/20* (2018.01); *A61B 5/441* (2013.01)

(58) Field of Classification Search
CPC ................................ G16H 50/20; A61B 5/441
See application file for complete search history.

(56) References Cited

U.S. PATENT DOCUMENTS

2003/0013994 A1    1/2003    Rubinstenn et al.
2003/0065278 A1    4/2003    Rubinstenn et al.
(Continued)

FOREIGN PATENT DOCUMENTS

JP    2014522990 A    9/2014
JP    2016522676 A    8/2016
(Continued)

OTHER PUBLICATIONS

Office Action mailed Nov. 18, 2024, in corresponding Japanese application No. 2023-560141, filed Apr. 29, 2022, 22 pages.
(Continued)

*Primary Examiner* — Maroun P Kanaan
(74) *Attorney, Agent, or Firm* — Christensen O'Connor Johnson Kindness PLLC

(57) ABSTRACT

In some embodiments, techniques for improving treatment outcomes are provided. A computing system measures at least one skin condition for a subject. The computing system receives a plurality of types of omics data for the subject. For each type of omics data, the computing system uses at least one classifier associated with the type of omics data to determine whether the subject is in at least one responder category. The computing system predicts treatment out-
(Continued)

comes for the at least one skin condition for the subject for a plurality treatments based on the at least one responder category. The computing system determines a skincare regimen based on the predicted treatment outcomes.

18 Claims, 3 Drawing Sheets

(56) References Cited

U.S. PATENT DOCUMENTS

| | | | |
|---|---|---|---|
| 2010/0185064 A1* | 7/2010 | Bandic | A61B 5/444 600/306 |
| 2011/0251872 A1 | 10/2011 | Wei | |
| 2014/0242599 A1 | 8/2014 | Budde et al. | |
| 2016/0016171 A1 | 1/2016 | Goel | |
| 2017/0035348 A1 | 2/2017 | Bandic et al. | |
| 2017/0098032 A1 | 4/2017 | Desai et al. | |
| 2018/0328945 A1* | 11/2018 | Nova | C12Q 1/6883 |
| 2019/0188809 A1 | 6/2019 | Jung et al. | |
| 2019/0220738 A1 | 7/2019 | Flank | |
| 2019/0228840 A1 | 7/2019 | Kamens et al. | |
| 2019/0292577 A1 | 9/2019 | Amini et al. | |
| 2020/0170564 A1 | 6/2020 | Jiang et al. | |
| 2020/0250866 A1 | 8/2020 | Balooch et al. | |
| 2020/0321074 A1 | 10/2020 | Tran | |
| 2021/0035185 A1 | 2/2021 | Lee et al. | |

FOREIGN PATENT DOCUMENTS

| | | |
|---|---|---|
| WO | 2014/208185 A1 | 4/2014 |
| WO | 2021/029332 A1 | 8/2020 |

OTHER PUBLICATIONS

French Written Opinion and Search Report mailed Apr. 6, 2022, issued in corresponding French Application No. FR2108018, filed Jul. 23, 2021, 7 pages.

Jiang, S. et al., "Biomarkers of an Autoimmune Skin Disease—Psoriasis", Genomics Proteomics Bioinformatics (2015) 13, pp. 224-233.

Pećina-Šlaus, N., et al., "Only one health, and so many omics," Cancer Cell International (2015) 15:64, pp. 1-7.

Boroni, M., et al., "Highly accurate skin-specific methylome analysis algorithm as a platform to screen and validate therapeutics for healthy aging," Clinical Epigenetics (2020) 12:105, pp. 1-16.

International Search Report and Written Opinion mailed Jul. 29, 2022, issued in corresponding International Application No. PCT/US2022/027110, filed Apr. 29, 2022, 13 pages.

Office Action mailed May 27, 2025, in corresponding Japanese application No. 2023-560141, filed Apr. 29, 2022, 22 pages.

\* cited by examiner

PREDICTING EFFICACIES AND IMPROVING SKINCARE TREATMENT OUTCOMES BASED ON RESPONDER/NON-RESPONDER INFORMATION

CROSS REFERENCE TO RELATED APPLICATIONS

This application is a National Stage of International Application No. PCT/US2022/027110, filed Apr. 29, 2022, which claims the benefit of Provisional Application No. 63/182,664, filed Apr. 30, 2021. This application also claims priority to French Patent Application No. 2108018, filed Jul. 23, 2021. The entire disclosures of these applications are hereby incorporated by reference herein for all purposes.

DESCRIPTION OF THE DRAWINGS

Many of the attendant advantages of this invention will become more readily appreciated as the same become better understood by reference to the following detailed description, when taken in conjunction with the accompanying drawings, wherein.

DETAILED DESCRIPTION

In some embodiments of the present disclosure, systems, devices, and/or methods are provided to predict efficacies of various skincare treatments to improve treatment outcomes based on responder/non-responder information determined from omics data.

The techniques disclosed herein provide a variety of technical improvements. As one non-limiting example, using classifiers for a plurality of types of omics data in order to automatically determine responder categories for a subject improves the accuracy of the determination of the responder categories, which is itself a technical improvement, and also further improves treatment outcomes for the subject since the treatments can be based on more accurate information. As another non-limiting example, considering responder categories that change over time also improves the accuracy of the determination of the responder categories, which is a technical improvement for similar reasons. As a further non-limiting example, measuring a clinical sign of aging after application of a skincare regimen and updating at least one classifier based on the measurement helps improve the performance of the at least one classifier, thereby allowing the generation of further-improved determinations of responder categories, and provide further improved treatment outcomes.

Figure 1:
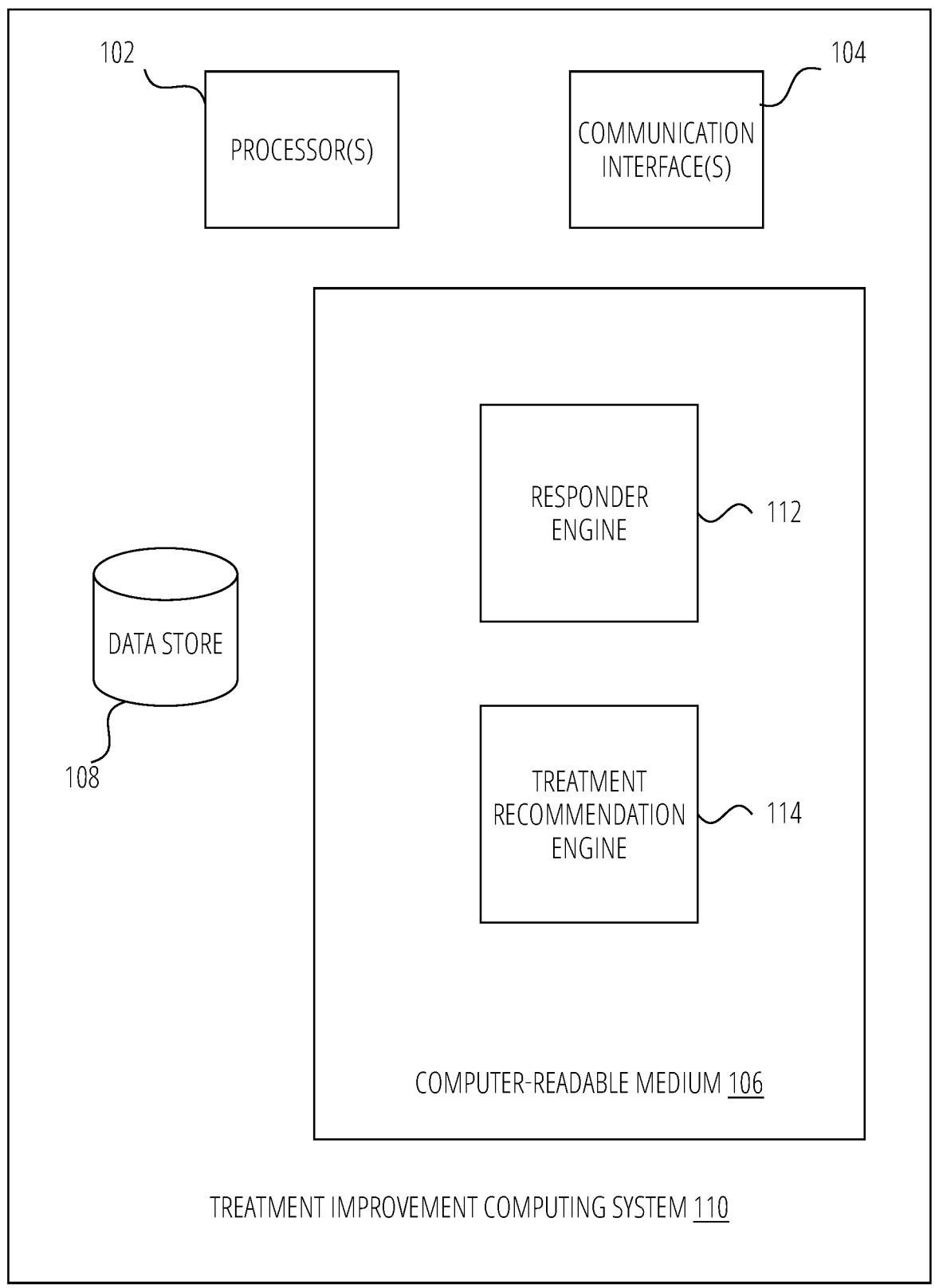
FIG. 1 is a block diagram that illustrates aspects of a non-limiting example embodiment of a treatment improvement computing system according to various aspects of the present disclosure.

FIG. 1 is a block diagram that illustrates aspects of a non-limiting example embodiment of a treatment improvement computing system according to various aspects of the present disclosure. The illustrated treatment improvement computing system 110 may be implemented by any computing device or collection of computing devices, including but not limited to a desktop computing device, a laptop computing device, a mobile computing device, a server computing device, a computing device of a cloud computing system, and/or combinations thereof. The treatment improvement computing system 110 is configured to use classifiers to process omics data in order to determine ideal skincare regimens for subjects to address clinical signs of aging, to address skin conditions including but not limited to acne or eczema, or any other skincare purpose.

As shown, the treatment improvement computing system 110 includes one or more processors 102, one or more communication interfaces 104, a data store 108, and a computer-readable medium 106.

In some embodiments, the processors 102 may include any suitable type of general-purpose computer processor. In some embodiments, the processors 102 may include one or more special-purpose computer processors or AI accelerators optimized for specific computing tasks, including but not limited to graphical processing units (GPUs), vision processing units (VPTs), and tensor processing units (TPUs).

In some embodiments, the communication interfaces 104 include one or more hardware and or software interfaces suitable for providing communication links between components. The communication interfaces 104 may support one or more wired communication technologies (including but not limited to Ethernet, FireWire, and USB), one or more wireless communication technologies (including but not limited to Wi-Fi, WiMAX, Bluetooth, 2G, 3G, 4G, 5G, and LTE), and/or combinations thereof.

As shown, the computer-readable medium 106 has stored thereon logic that, in response to execution by the one or more processors 102, cause the treatment improvement computing system 110 to provide a responder engine 112 and a treatment recommendation engine 114.

As used herein, "computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

In some embodiments, the responder engine 112 is configured to determine whether a given subject is in a responder category or a non-responder category for various ingredients based on omics data obtained for the given subject. In some embodiments, the treatment recommendation engine 114 is configured to determine a skincare regimen for a given subject based on the responder categories determined by the responder engine 112. The responder engine 112 may use omics data stored in the data store 108, and/or classifiers stored in the data store 108. The treatment recommendation engine 114 may also use information stored in the data store 108 for its processing.

Further description of the configuration of each of these components is provided below.

As used herein, "engine" refers to logic embodied in hardware or software instructions, which can be written in one or more programming languages, including but not limited to C, C++, C#, COBOL, JAVA™, PHP, Perl, HTML, CSS, Javascript, VBScript, ASPX, Go, and Python. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 2:
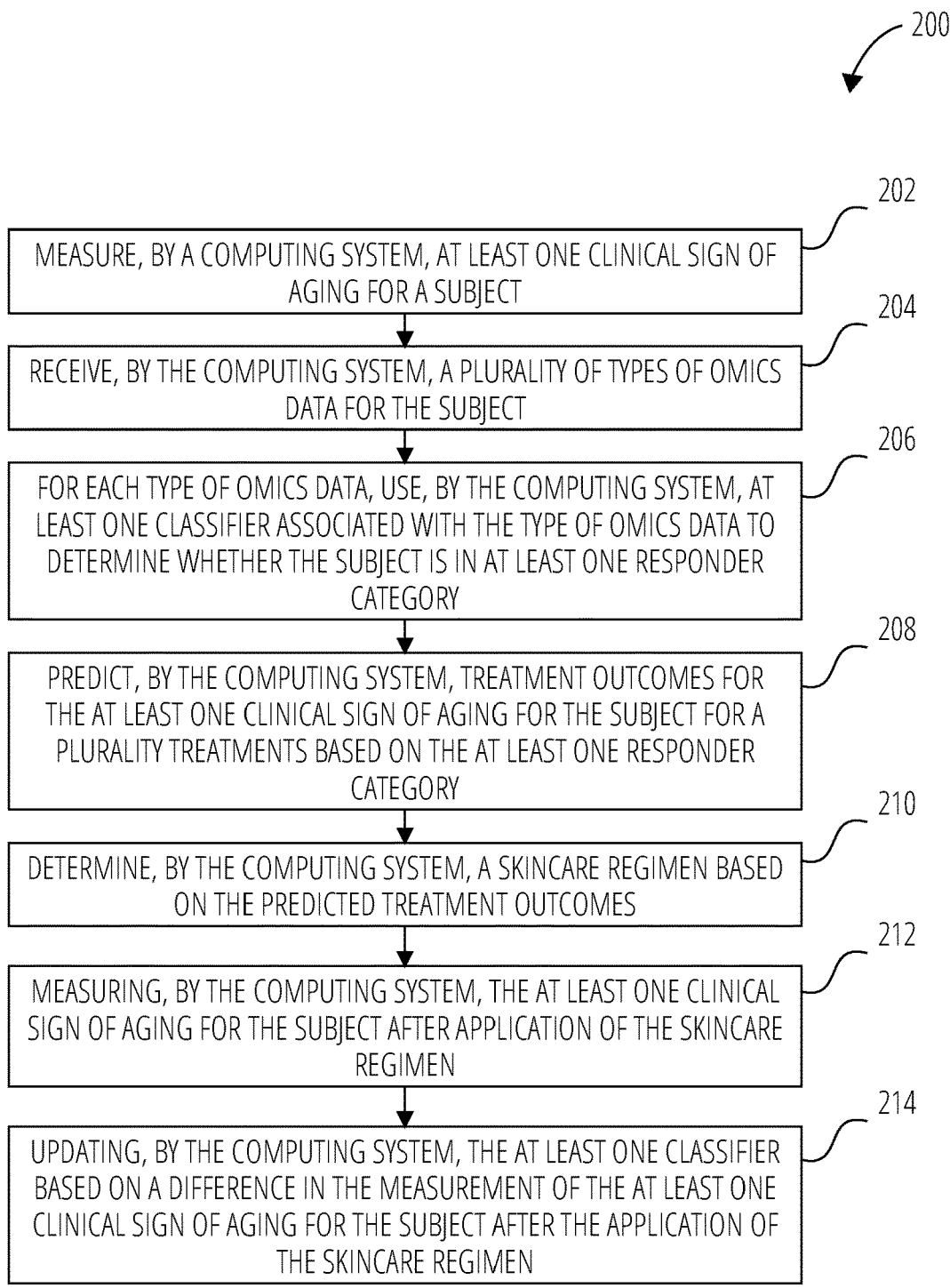
FIG. 2 is a flowchart that illustrates a non-limiting example embodiment of a method of improving aging treatment outcomes according to various aspects of the present disclosure.

FIG. 2 is a flowchart that illustrates a non-limiting example embodiment of a method of improving aging treatment outcomes according to various aspects of the present disclosure.

At block 202, a computing system measures at least one clinical sign of aging for a subject. Clinical signs of aging may be any type of age-related change in skin condition that is clinically observable, including but not limited to shiny skin, rough skin, uneven skin tone, eye wrinkles, photo aging, loss of elasticity, and dilated pores. The computing system may measure the at least one clinical sign of aging using any suitable technique, including but not limited to computer vision analysis of an image or three-dimensional scan of the subject, providing a questionnaire for completion by the subject, and providing a questionnaire for completion by a clinician observing the subject.

At block 204, the computing system receives a plurality of types of omics data for the subject. The computing system may itself collect the omics data, may receive the omics data from another device that samples the omics data from the subject, or may receive the omics data as input from the subject or a clinician. Any types of omics data that reflects useful information regarding the subject may be used, including, but not limited to:
  Genomic data
    Analysis of genome structure of organisms as a whole
    May be gathered using next-generation sequencing technologies
  Exomic data
    Exomes are the protein coding content of the genetic code, the part of the genome formed by exons. The exome constitutes 1-2% of the genome.
    Solution based: In solution-based, whole-exome sequencing (WES), DNA samples are fragmented and biotinylated oligonucleotide probes (baits) are used to selectively hybridize to target regions in the genome.
    Array based: Array-based methods are similar except that the probes are bound to a high-density microarray.
  Transcriptomic data
    Analysis of all the transcripts being produced at any one time in an individual, disease state or cell tells us which genes are switched on or off.
    May be gathered using cDNA microarrays or RNA-seq techniques
    Reflected in different rates of transcription (synthesis of RNA molecules in a specific organism, tissue or cell type at a given time)
  Epigenomic data
    Chemical marks on the DNA, regulating whether the gene is turned "on" or "off"
  Proteomic data
    Proteins produced by a particular genome
  Metabolomic data
    Metabolites produced by a single organism
    May be obtained using NMR spectroscopy
  Microbiomic data
    Microorganisms (and their genes) living in a specific environment (e.g., gut, skin)
  Metagenomic data
    The genes of microorganisms in a specific environment
  Hormone data
    May include estrogen, progesterone, testosterone, cortisol, melatonin, serotonin, growth hormone, leptin, ghrelin, and insulin
    May be measured using a blood test or saliva test
    Hormone levels will change over time and indicate points within a physiological cycle, such as a menstrual cycle At block 206, the computing system uses, for each type of omics data, at least one classifier associated with the type of omics data to determine whether the subject is in at least one responder category. A responder category indicates whether the subject will respond to a particular skincare product ingredient associated with the responder category. For example, responder categories may include, but are not limited to, a retinol responder category, a proxylane responder category, a vitamin C responder category, a hyaluronic acid responder category, an endolysin responder category, and a lipohydroxy acid (LHA) responder category.

In some embodiments, separate classifiers may be trained for each type of omics data and each responder category. In some embodiments, a single classifier may be trained to receive multiple types of omics data to determine a single responder category. In some embodiments, a single classifier may be trained for each type of omics data, but may provide categorization for multiple responder categories. Any suitable type or combination of types of classifier may be used, including but not limited to decision trees, naïve Bayes classifiers, k-nearest neighbors classifiers, support vector machines, and artificial neural networks. The classifiers may be trained using any suitable technique, including but not limited to determining a set of labeled training data using subjects for which ground truth responder category information is known, and training the classifiers using the labeled training data via a technique including but not limited to gradient descent.

In addition to the above, other information could be used to determine responder categories. For example, in some embodiments, indications of time dependent modifications in DNA methylation (DNAm) are used to estimate the molecular versus the chronological age of human tissues. See e.g., Boroni, M., Zonari, A., Reis de Oliveira, C. et al. "Highly accurate skin-specific methylome analysis algorithm as a platform to screen and validate therapeutics for healthy aging," Clin Epigenet 12, 105 (2020); available at https://doi.org/10.1186/s13148-020-00899-1; incorporated by reference herein in its entirety). As another example, in some embodiments, indications of genetic susceptibility to UV damage is used to classify and individual as a responder for sunscreen protection (See, e.g., Lear J T et al., "Detoxifying Enzyme Genotypes and Susceptibility to Cutaneous Malignancy," Br J Dermatol. 2000 January; 142(1):8-15 doi: 10.1046/j.1365-2133.2000.03339.x. PMID: 10651688; available at https://pubmed.ncbi.nlm.nih.gov/10651688/(describing how polymorphisms in detoxifying enzyme genes are important in determining susceptibility to skin cancer, incorporated by reference herein it its entirety). As still another example, in some embodiments, one or more genomic, transcriptomic, proteomic, or metabolomics biomarkers for psoriasis are used to classify an individual as a responder for certain skincare products. (See, e.g., Jiang S et al., "Biomarkers of An Autoimmune Skin Disease—Psoriasis." *Genomics Proteomics Bioinformatics.* 2015; 13(4): 224-233; doi:10.1016/j.gpb.2015.04.002; incorporated by reference herein in its entirety).

At block 208, the computing system predicts treatment outcomes for the at least one clinical sign of aging for the subject for a plurality treatments based on the at least one responder category. In some embodiments, the computing system may be configured with information regarding effects of various skincare treatments for various responder categories. For example, the computing system may be configured to know how a given skincare treatment will affect a given clinical sign of aging for subjects in a responder category for an ingredient of the given skincare treatment versus subjects who are not in the responder category for the ingredient of the given skincare treatment.

At block 210, the computing system determines a skincare regimen based on the predicted treatment outcomes. For example, the computing system may determine one or more products that have ingredients that were determined at block 208 to improve treatment outcomes for the subject. In some embodiments, the computing system may provide an indication of the skincare regimen to the subject or to a clinician to recommend the products for use. In some embodiments, the computing system may provide an indication of the skincare regimen to a device to compound a custom skincare product that includes the ingredients determined to improve treatment outcomes. In some embodiments, the computing system may provide a visualization that illustrates effects of the skincare regimen, based on the determination of the responder groups to which the subject belongs and/or other characteristics of the subject.

At optional block 212, the computing system measures the at least one clinical sign of aging for the subject after application of the skincare regimen. The computing system may use a similar technique to measure the at least one clinical sign of aging as used in block 202. At optional block 214, the computing system updates the at least one classifier based on a difference in the measurement of the at least one clinical sign of aging for the subject after the application of the skincare regimen. For example, the difference in measurement of the at least one clinical sign of aging may be used to determine a ground truth of whether the subject was in a responder category or a non-responder category for the ingredients used in the skincare regimen (e.g., if there was improvement, the ground truth would be that the subject was in the responder category, and if there was not improvement or less than expected improvement, the ground truth would be that the subject was in the non-responder category). This ground truth may then be used with the omics data for the subject to re-train the appropriate classifiers. Optional block 212 and optional block 214 are illustrated as optional because in some embodiments, this data collection and re-training of the classifiers may not be performed.

While the discussion of method 200 above primarily includes treatments for affecting clinical signs of aging, in some embodiments, treatments for other conditions may be considered. For example, the responder categories may be used to determine a skincare regimen to address a medical condition including but not limited to acne or eczema. As another example, the responder categories may be used to determine a skincare regimen to address skin tone management.

Figure 3:
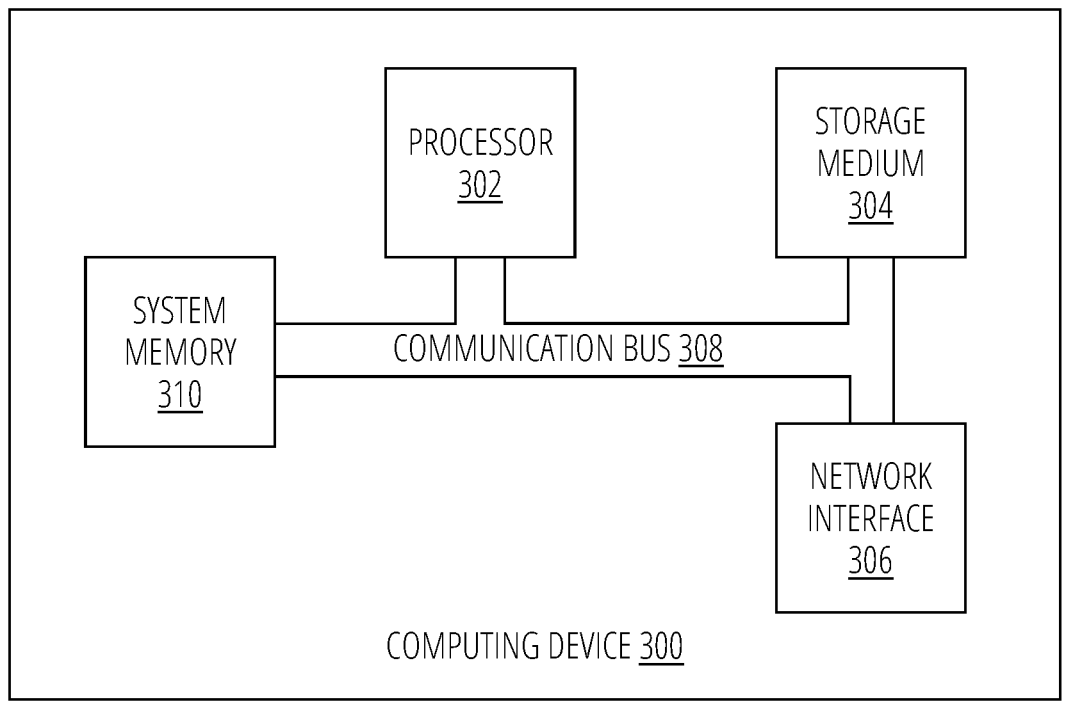
FIG. 3 is a block diagram that illustrates a non-limiting example embodiment of a computing device appropriate for use as a computing device with embodiments of the present disclosure.

FIG. 3 is a block diagram that illustrates aspects of an exemplary computing device 300 appropriate for use as a computing device of the present disclosure. While multiple different types of computing devices were discussed above, the exemplary computing device 300 describes various elements that are common to many different types of computing devices. While FIG. 3 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Some embodiments of a computing device may be implemented in or may include an application-specific integrated circuit (ASIC), a field-programmable gate array (FPGA), or other customized device. Moreover, those of ordinary skill in the art and others will recognize that the computing device 300 may be any one of any number of currently available or yet to be developed devices.

In its most basic configuration, the computing device 300 includes at least one processor 302 and a system memory 310 connected by a communication bus 308. Depending on the exact configuration and type of device, the system memory 310 may be volatile or nonvolatile memory, such as read only memory ("ROM"), random access memory ("RAM"), EEPROM, flash memory, or similar memory technology. Those of ordinary skill in the art and others will recognize that system memory 310 typically stores data and/or program modules that are immediately accessible to and/or currently being operated on by the processor 302. In this regard, the processor 302 may serve as a computational center of the computing device 300 by supporting the execution of instructions.

As further illustrated in FIG. 3, the computing device 300 may include a network interface 306 comprising one or more components for communicating with other devices over a network. Embodiments of the present disclosure may access basic services that utilize the network interface 306 to perform communications using common network protocols. The network interface 306 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 306 illustrated in FIG. 3 may represent one or more wireless interfaces or physical communication interfaces described and illustrated above with respect to particular components of the computing device 300.

In the exemplary embodiment depicted in FIG. 3, the computing device 300 also includes a storage medium 304. However, services may be accessed using a computing device that does not include means for persisting data to a local storage medium. Therefore, the storage medium 304 depicted in FIG. 3 is represented with a dashed line to indicate that the storage medium 304 is optional. In any event, the storage medium 304 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computing devices that include a processor 302, system memory 310, communication bus 308, storage medium 304, and network interface 306 are known and commercially available. For ease of illustration and because it is not important for an understanding of the claimed subject matter, FIG. 3 does not show some of the typical components of many computing devices. In this regard, the computing device 300 may include input devices, such as a keyboard, keypad, mouse, microphone, touch input device, touch screen, tablet, and/or the like. Such input devices may be coupled to the computing device 300 by wired or wireless connections including RF, infrared, serial, parallel, Bluetooth, Bluetooth low energy, USB, or other suitable connections protocols using wireless or physical connections. Similarly, the computing device 300 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of improving treatment outcomes, the method comprising:
    measuring, by a computing system, at least one skin condition for a subject to obtain a first measurement;
    receiving, by the computing system, a plurality of types of omics data for the subject;
    for each type of omics data, using, by the computing system, at least one classifier associated with the type of omics data to determine whether the subject is in at least one responder category by providing the type of omics data as input to the at least one classifier, wherein the responder category indicates whether the subject is predicted to respond to a particular skincare product ingredient associated with the responder category;
    predicting, by the computing system, treatment outcomes for the at least one skin condition for the subject for a plurality of treatments based on the at least one responder category using stored data indicating how a given skincare treatment will affect a given clinical sign of aging for subjects in the at least one responder category;
    determining, by the computing system, a skincare regimen based on the predicted treatment outcomes;
    measuring, by the computing system, the at least one skin condition for the subject after application of the skincare regimen to obtain a second measurement; and
    updating, by the computing system, the at least one classifier based on a difference between the first measurement and the second measurement.

2. The computer-implemented method of claim 1, wherein the types of omics data include two or more of genomic data, exomic data, transcriptomic data, epigenomic data, proteomic data, metabolomic data, and microbiomic data.

3. The computer-implemented method of claim 1, wherein the at least one responder category includes at least one of:
    a retinol responder category;
    a proxylane responder category;
    a vitamin C responder category;
    a hyaluronic acid responder category;
    an endolysin responder category; and
    a lipohydroxy acid (LHA) responder category.

4. The computer-implemented method of claim 1, wherein at least one responder category changes over time for the subject.

5. The computer-implemented method of claim 4, wherein the at least one responder category that changes over time for the subject changes based on a date in a physiological cycle for the subject.

6. The computer-implemented method of claim 5, wherein the physiological cycle for the subject is a menstrual cycle.

7. The computer-implemented method of claim 1, wherein the at least one skin condition includes at least one of a clinical sign of aging, a medical condition, and a skin tone.

8. The computer-implemented method of claim 1, further comprising:
    providing, by the computing system, the type of omics data as input to the updated at least one classifier to create an updated determination of whether the subject is in the at least one responder category;
    predicting, by the computing system, updated treatment outcomes for the at least one skin condition for the subject for the plurality of treatments based on the updated determination;
    determining, by the computing system, an updated skincare regimen based on the predicted updated treatment outcomes; and
    applying the updated skincare regimen.

9. A computing system, comprising:
    a responder engine including computational circuitry configured to:
        measure at least one skin condition for a subject to obtain a first measurement;
        receive a plurality of types of omics data for the subject; and
        for each type of omics data, use at least one classifier associated with the type of omics data to determine whether the subject is in at least one responder category by providing the type of omics data as input to the at least one classifier, wherein the responder category indicates whether the subject is predicted to respond to a particular skincare product ingredient associated with the responder category;
    a treatment recommendation engine including computational circuitry configured to:
        predict treatment outcomes for the at least one skin condition for the subject for a plurality of treatments based on the at least one responder category using stored data indicating how a given skincare treatment will affect a given clinical sign of aging for subjects in the at least one responder category;

determine a skincare regimen based on the predicted treatment outcomes;

measure the at least one skin condition for the subject after application of the skincare regimen to obtain a second measurement; and update the at least one classifier based on a difference between the first measurement and the second measurement.

10. The computing system of claim 9, wherein the types of omics data include two or more of genomic data, exomic data, transcriptomic data, epigenomic data, proteomic data, metabolomic data, and microbiomic data.

11. The computing system of claim 9, wherein the at least one responder category includes at least one of:
 a retinol responder category;
 a proxylane responder category;
 a vitamin C responder category;
 a hyaluronic acid responder category;
 an endolysin responder category; and
 a lipohydroxy acid (LHA) responder category.

12. The computing system of claim 9, wherein at least one responder category changes over time for the subject.

13. The computing system of claim 12, wherein the at least one responder category that changes over time for the subject changes based on a date in a physiological cycle for the subject.

14. The computing system of claim 13, wherein the physiological cycle for the subject is a menstrual cycle.

15. The computing system of claim 13, wherein the at least one skin condition includes at least one of a clinical sign of aging, a medical condition, and a skin tone.

16. A non-transitory computer-readable medium having computer-executable instructions stored thereon that, in response to execution by one or more processors of a computing system, cause the computing system to perform actions comprising:

measuring, by the computing system, at least one skin condition for a subject to obtain a first measurement;

receiving, by the computing system, a plurality of types of omics data for the subject;

for each type of omics data, using, by the computing system, at least one classifier associated with the type of omics data to determine whether the subject is in at least one responder category by providing the type of omics data as input to the at least one classifier, wherein the responder category indicates whether the subject is predicted to respond to a particular skincare product ingredient associated with the responder category;

predicting, by the computing system, treatment outcomes for the at least one skin condition for the subject for a plurality of treatments based on the at least one responder category using stored data indicating how a given skincare treatment will affect a given clinical sign of aging for subjects in the at least one responder category;

determining, by the computing system, a skincare regimen based on the predicted treatment outcomes;

measuring, by the computing system, the at least one skin condition for the subject after application of the skincare regimen to obtain a second measurement; and updating, by the computing system, the at least one classifier based on a difference between the first measurement and the second measurement.

17. The non-transitory computer-readable medium of claim 16, wherein the types of omics data include two or more of genomic data, exomic data, transcriptomic data, epigenomic data, proteomic data, metabolomic data, and microbiomic data.

18. The non-transitory computer-readable medium of claim 16, wherein the at least one responder category includes at least one of:
 a retinol responder category;
 a proxylane responder category;
 a vitamin C responder category;
 a hyaluronic acid responder category;
 an endolysin responder category; and
 a lipohydroxy acid (LHA) responder category.

* * * * *